(12) United States Patent
Yan

(10) Patent No.: US 11,090,510 B2
(45) Date of Patent: Aug. 17, 2021

(54) METHOD FOR TRACKING TUMOR LOCATION AND RADIOTHERAPY APPARATUS

(71) Applicant: OUR NEW MEDICAL TECHNOLOGIES, Guangdong (CN)

(72) Inventor: Hao Yan, Guangdong (CN)

(73) Assignee: OUR NEW MEDICAL TECHNOLOGIES, Guangdong (CN)

(*) Notice: Subject to any disclaimer, the term of this patent is extended or adjusted under 35 U.S.C. 154(b) by 49 days.

(21) Appl. No.: 16/218,675

(22) Filed: Dec. 13, 2018

(65) Prior Publication Data

US 2019/0111283 A1    Apr. 18, 2019

Related U.S. Application Data

(63) Continuation-in-part of application No. PCT/CN2016/085907, filed on Jun. 15, 2016.

(51) Int. Cl.
*A61N 5/10* (2006.01)
*A61B 6/12* (2006.01)
*A61B 6/00* (2006.01)

(52) U.S. Cl.
CPC .............. *A61N 5/1049* (2013.01); *A61B 6/12* (2013.01); *A61B 6/4291* (2013.01); *A61B 6/483* (2013.01);
(Continued)

(58) Field of Classification Search
CPC .... A61N 5/1049; A61N 5/1067; A61N 5/107; A61N 2005/1054; A61N 2005/1061;
(Continued)

(56) References Cited

U.S. PATENT DOCUMENTS 8,670,523 B2 * 3/2014 Yan .................. A61N 5/107
378/20
8,989,469 B2    3/2015 Fahimian et al.
(Continued)

FOREIGN PATENT DOCUMENTS

| CN | 102264301 A | 11/2011 |
| CN | 105374654 A | 3/2016 |
| WO | WO2016/172312 A1 | 10/2016 |

OTHER PUBLICATIONS

International Search Report of PCT/CN2016/085907 dated Mar. 15, 2017.

*Primary Examiner* — Blake C Riddick
(74) *Attorney, Agent, or Firm* — Daniel J. Chalker; Edwin S. Flores; Chalker Flores, LLP

(57) ABSTRACT

Provided are a method for tracking tumor location and a radiotherapy apparatus, relating to the field of medical equipment technology. The method is applied to a radiotherapy apparatus comprising a first detector and at least one radiation source, and comprises emitting, from the radiation source, ray beams having a predetermined intensity, the ray beams being partially scattered after passing through a body lesion; receiving, by the first detector, a portion of scattered ray beams to acquire scattering data of the lesion; determining a relative location relationship between the lesion and a target region according to the acquired scattering data; and adjusting at least one of the ray beam intensity, lesion location and target region location according to the determined relative location relationship, such that the lesion receives irradiation of the ray beams having an adjusted predetermined intensity at the target region location.

9 Claims, 2 Drawing Sheets

(52) U.S. Cl.
CPC ........... *A61N 5/107* (2013.01); *A61N 5/1067* (2013.01); *A61B 6/482* (2013.01); *A61B 6/5217* (2013.01); *A61N 2005/1054* (2013.01); *A61N 2005/1061* (2013.01); *A61N 2005/1072* (2013.01); *A61N 2005/1074* (2013.01)

(58) Field of Classification Search
CPC .... A61N 2005/1072; A61N 2005/1074; A61B 6/12; A61B 6/4291; A61B 6/483; A61B 6/482; A61B 6/5217
See application file for complete search history.

(56) References Cited

U.S. PATENT DOCUMENTS

| | | | |
|---|---|---|---|
| 9,339,243 B2* | 5/2016 | Zhang | A61B 6/025 |
| 2005/0220265 A1* | 10/2005 | Besson | A61B 6/488 378/16 |
| 2009/0161818 A1* | 6/2009 | Sakurai | A61N 5/1048 378/15 |
| 2009/0175418 A1* | 7/2009 | Sakurai | A61N 5/1048 378/98.5 |
| 2010/0080354 A1* | 4/2010 | Fu | G06T 5/50 378/65 |
| 2010/0106005 A1* | 4/2010 | Karczmar | A61N 7/02 600/411 |
| 2012/0014501 A1* | 1/2012 | Pelc | G06T 7/0012 378/9 |
| 2013/0060134 A1 | 3/2013 | Eshima et al. | |
| 2013/0188856 A1* | 7/2013 | Adler, Jr. | A61N 5/107 382/132 |
| 2016/0038768 A1* | 2/2016 | Liu | A61N 5/1082 378/62 |
| 2016/0114191 A1* | 4/2016 | Sankey | A61N 5/1049 378/62 |
| 2018/0015306 A1* | 1/2018 | Maurer, Jr. | A61B 6/4014 |
| 2018/0140265 A1* | 5/2018 | Chu | A61N 5/1049 |
| 2018/0236267 A1* | 8/2018 | Kuang | A61N 5/1039 |
| 2019/0126070 A1* | 5/2019 | Hsieh | A61N 5/1067 |

* cited by examiner

METHOD FOR TRACKING TUMOR LOCATION AND RADIOTHERAPY APPARATUS

PRIORITY CLAIM AND CROSS-REFERENCE TO RELATED APPLICATIONS

This application is a U.S. National Stage Application of and claims priority to International Application No. PCT/CN2016/085907, filed on Jun. 15, 2016, the contents of which are incorporated by reference herein in their entirety.

FIELD OF THE INVENTION

The present disclosure relates to the technical field of medical instruments, and more particularly, to a method for tracking tumor location and a radiotherapy apparatus.

BACKGROUND OF THE INVENTION

In radiation therapy, precise localization of a tumor location is necessary for accurate radiotherapy. Currently, tumor location is usually tracked by monitoring the signal data of external surrogate associated with the lesion site, such as the motion of a marker on the surface of patient body, the change in gas volume during the respiration of patient, or the change in patient's abdominal pressure. Through these manners, the movement of the tumor location are predicted. However, these external surrogate signal data has relatively high uncertainty, therefore, the tumor movement could not be characterized accurately, resulting in relatively low accuracy and reliability when tracking the tumor location. In addition, in the practical applications, the 3D spatial location of a tumor could be obtained through an inverse calculation of the 2D position result by implanting a plurality of metal markers into the tumor region, conducing projectional imaging and acquiring the 2D position of the tumor in two X-ray projectional image. Yet in this manner, the implantation of the plurality of metal markers brings about additional surgical pains to the patient and is likely to induce a "pneumothorax" condition. Moreover, the metal markers may move inside the body, affecting the accuracy and reliability in tracking the tumor location.

SUMMARY OF THE INVENTION

In view of the above mentioned fact, the present disclosure provides a method for tracking tumor location and a radiotherapy apparatus, for the purpose of solving the technical problem that the accuracy and reliability of the existing tracking method of tumor location are relatively low.

According to an embodiment of the present disclosure, there is provided a method for tracking tumor location applied to a radiotherapy apparatus, the apparatus comprising a first detector and at least one radiation source, wherein the radiation source, a body lesion and the first detector are not located on a straight line; the method comprising: emitting, from the radiation source, ray beams having a predetermined intensity, the ray beams being partially scattered after passing through the body lesion; receiving, by the first detector, a portion of scattered ray beams to acquire scattering data of the lesion; determining a relative location relationship between the lesion and a target region based on the acquired scattering data; and adjusting at least one of the intensity of ray beams, a lesion location and a target region location according to the determined relative location relationship, such that the lesion receives the irradiation of the ray beams having an adjusted predetermined intensity at the target region location.

In some embodiments, the first detector comprises at least one first detector unit; the method for tracking tumor location, prior to said receiving, by the first detector, a portion of scattered ray beams to acquire scattering data of the lesion before the first detector receives a portion of ray beams that are scattered when the ray beams pass through the lesion region, further comprises: filtering the ray beams, such that the first detector unit receives the ray beams having specific scattering angles.

In some embodiments, the first detector comprises at least one first detector unit; said receiving, by the first detector, a portion of scattered ray beams to acquire scattering data of the lesion comprises: receiving, by the first detector unit, a portion of ray beams that are scattered when the ray beams pass through the lesion region, distinguishing and classifying the received portion of ray beams based on energy, and acquiring scattering data of the lesion region according to the classification result.

In some embodiments, the at least one radiation source is a therapeutic radiation source, or the at least one radiation source comprises at least one therapeutic radiation source and at least one diagnostic radiation source.

In some embodiments, when the radiation source includes a plurality of radiation sources, the plurality of radiation sources are used at different reference moments.

In some embodiments, the radiotherapy apparatus further comprises a second detector; the radiation source, the body lesion and the second detector are located on a straight line; the second detector is configured to receive ray beams that are transmitted when the ray beams emitted from the radiation source pass through the body lesion, to acquire transmission data of the lesion; the method for tracking tumor location further comprises: receiving, by the second detector, ray beams that are transmitted when ray beams emitted from the radiation source pass through the body lesion, to acquire transmission data of the lesion; and determining a relative location relationship between the lesion and the target region according to the acquired scattering data and transmission data.

According to another embodiment of the present disclosure, there is provided a radiotherapy apparatus, comprising a first detector and at least one radiation source, and at least one of a ray beam intensity adjusting mechanism, a bed driving mechanism and a radiation source driving mechanism, wherein the radiation source, a body lesion and the first detector are not located on a straight line; the radiation source is configured to emit ray beams having a predetermined intensity, the ray beams being partially scattered after passing through the body lesion; the first detector is configured to receive a portion of scattered ray beams to acquire scattering data of the lesion region; the radiotherapy apparatus further comprises a processor configured to determine a relative location relationship between the lesion and a target region according to the scattering data acquired by the first detector; the ray beam intensity adjusting mechanism is configured to adjust the intensity of ray beams according to the relative location relationship between the lesion and the target region determined by the processor; the bed driving mechanism is configured to adjust a lesion location according to the relative location relationship between the lesion and the target region determined by the processor; the radiation source driving mechanism is configured to adjust a target region location according to the relative location relationship between the lesion and the target region determined by the processor.

In some embodiments, the first detector comprises at least one first detector unit; the radiotherapy apparatus further comprises a filter unit configured to filter the scattered ray beams, such that a specific first detector unit receives the scattered ray beams having specific scattering angles.

In some embodiments, the first detector comprises at least one first detector unit; the processor is further configured to distinguish and classify the scattered ray beams received by the first detector unit based on energy, and acquire scattering data of the lesion region according to the classification result.

In some embodiments, the at least one radiation source is a therapeutic radiation source, or the at least one radiation source comprises at least one therapeutic radiation source and at least one diagnostic radiation source.

According to the method for tracking tumor location and the radiotherapy apparatus provided by the present disclosure, by means of the steps of receiving, by the detector, the scattering data when the ray beams of the radiation source pass through the lesion location, determining the relative location relationship between the lesion and the target region, and adjusting at least one of the intensity of ray beams, the lesion location and the target region location according to the relative location relationship between the lesion and the target region location, the lesion receives the irradiation of the ray beams having an adjusted predetermined intensity at the target region. As such, fluctuations and errors in the intensity of the ray beams are avoided, and accurate therapy is achieved. Therefore, the tumor location could be precisely tracked and the radiotherapy location could be accurately adjusted, and therefore the lesion portion which is partially or completely out of the target region location could be treated effectively and the accuracy and reliability of the tumor treatment are improved.

BRIEF DESCRIPTION OF THE DRAWINGS

In order to illustrate the technical solutions in the embodiments provided by the present disclosure more clearly, a brief introduction on the accompany drawings that may be used in the detailed description of the embodiments is given. Apparently, the drawings as described below are merely for illustrating some embodiments of the present disclosure, and other drawings could be obtained by those of ordinary skilled in the art according to these drawings without any creative labor.

DETAILED DESCRIPTION OF THE INVENTION

The technical solutions of the present disclosure will be further described below in detail in conjunction with the drawings and the specific embodiments. It is apparent that the described embodiments are only a portion of the embodiments of the present disclosure, but not all of them. All other embodiments obtained by those of ordinary skill in the art based on the embodiments of the present disclosure without any creative effort shall fall within the protection scope of the present disclosure.

In the description of the present disclosure, it should be understood that, the terms "first", "second" and the like are used for a descriptive purpose only and shall not be construed as indicating or implying relative importance. Unless otherwise specified and limited, it should be noted that the expressions "connected with each other" and "connected to/with" in the present description should be understood in a broad manner. For example, a connection may be fixed connection, detachable connection or integrated connection; or may be mechanical connection, or electrical connection; or may be direct connection, or indirect connection via an intermediate. Those of ordinary skill in the art can understand the specific meaning of the above expressions in accordance with specific conditions. In the description of the present disclosure, unless otherwise specified, "a plurality of" means a number of two or more.

Any process or method descriptions described in flowcharts or otherwise herein may be understood as representing modules, segments or portions of codes that include one or more executable instructions for implementing the steps of a particular logical function or process. In addition, the scope of the preferred embodiments of the present disclosure includes further implementations in which functions may be performed in a substantially simultaneous form or an inverse sequence according to the involved functions, rather than the sequence as shown or discussed, which should be understood by those skilled in the art.

In an embodiment of the present disclosure, a method for tracking tumor location is applied to a radiotherapy apparatus comprising radiation source and a first detector. The radiation source, a body lesion and the first detector are not located on a straight line. The radiation source is configured to emit ray beams having a predetermined intensity, and the ray beams pass through the body lesion to form scattered ray beams.

Figure 1:
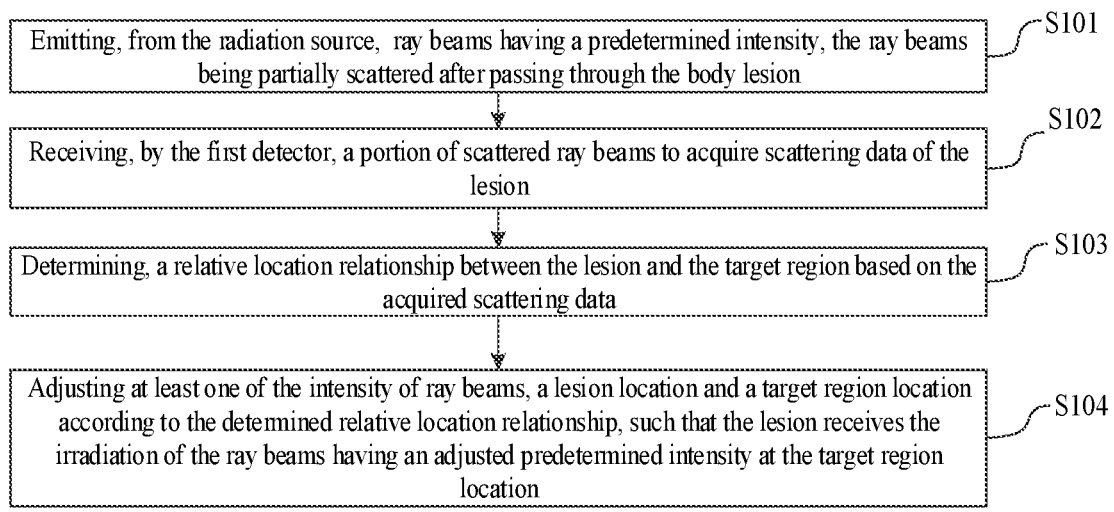
FIG. 1 is a schematic flowchart of a method for tracking tumor location according to an embodiment of the present disclosure.

FIG. 1 is a schematic flowchart of a method for tracking tumor location in an embodiment of the present disclosure. As shown in FIG. 1, the method for tracking tumor location includes the following steps S101-S104.

In step S101, the radiation source emits ray beams having a predetermined intensity, the ray beams being partially scattered after passing through the body lesion.

In the present embodiment, the radiotherapy apparatus may include one or more therapeutic heads. Each therapeutic head includes one or more radiation sources. The radiation source may be a therapeutic radiation source, such as an isotope radiation source or an accelerator radiation source, that emits ray beams having a predetermined intensity to treat a lesion. The radiotherapy apparatus may further include a diagnostic radiation source, such as a bulb tube. The diagnostic radiation source may emit ray beams having a predetermined intensity in real time to image a lesion location. In some embodiments, the radiotherapy apparatus includes a plurality of therapeutic heads which could be used at different reference moments. For example, the reference using moments may be set to be spaced by a short time of 0.1 second, 0.2 second or 0.3 second, so as to prevent the plurality of therapeutic heads from simultaneously emitting ray beams to interfere with each other.

In step S102, the first detector receives a portion of scattered ray beams to acquire scattering data of the lesion.

In the present embodiment, the first detector is a high-sensitivity optical detection device configured to receive a portion of ray beams that are scattered when passing through the body lesion, to acquire scattering data of the body lesion, that is, the intensity data of the scattered ray beams. The first detector includes one or more first detector units which are configured to receive the scattered ray beams respectively. The detector acquires the scattering data of the lesion according to the scattered ray beams received by each detector unit.

In the implementations of the present disclosure, the radiation source may emit the ray beams periodically or continuously. In the embodiments of the present disclosure, explanations are made by taking radiation source emitting the ray beams periodically as an example, and this emitting manner is merely used for illustration, not limitation. In the case where the radiation source emits ray beams continuously, the rays emitted from the radiation source may be rays for treatment. At this time, the first detector may receive, at a predetermined time interval, the ray beams emitted from the radiation source, or continuously receive the ray beams emitted from the radiation source. In both cases, the intensity of the ray beams could be adjusted according to the practical requirement. As such, by adjusting the predetermined intensity of the ray beams, it means adjusting the intensity of next moments or time period based on practical requirement, or adjusting the intensity of next moments or time period based on the relative location relationship between the lesion and the target region as determined, or both.

Exemplarily, before the first detector receives a portion of ray beams that are scattered when the ray beams pass through the lesion region, the ray beams may also be filtered through a filter grid/lattice or a small-pore ray filter, such that the first detector unit receives ray beams having specific scattering angles. As such, the spatial distinguishing capability of the detector is achieved, the mutual interference among ray beams at different scattering angles is avoided, the accuracy and reliability of the scattering data as finally acquired are improved, and the accuracy and reliability of tracking the tumor location are also improved.

In step S103, a relative location relationship between the lesion and the target region is determined according to the acquired scattering data.

In the present embodiment, according to the acquired scattering data, that is, ray intensity data of the scattered ray beams, the relative location relationship between the lesion and the target region could be determined: the lesion completely falls within the target region, or is partially out of the target region or completely out of the target region, so as to subsequently determine whether the relative location relationship needs to be adjusted.

In step S104, at least one of the intensity of ray beams, a lesion location and a target region location is adjusted according to the determined relative location relationship, such that the lesion receives the irradiation of the ray beams having an adjusted predetermined intensity at the target region location.

In the present embodiment, when the lesion completely falls within the target region, the intensity of the ray beams of the radiation source may be adjusted by the ray beam intensity adjusting mechanism according to the intensity of the ray beams received by the lesion at the target region location in the previous one or two cycles or previous time period, such that in the next cycle or time period, the lesion receives the irradiation of the ray beams having an adjusted predetermined intensity at the target location, thereby avoiding fluctuations and errors in the intensity of the ray beams and achieving precise therapy.

In the present embodiment, when the lesion is partially out of the target region, the lesion region location may be adjusted by a bed driving mechanism, or the target region location may be adjusted by a radiation source driving mechanism, such that in the next cycle or time period, the lesion receives the irradiation of ray beams having an adjusted predetermined intensity within the target region location. Therefore, the tumor location could be precisely tracked, the radiotherapy location could be accurately adjusted, and therefore the lesion portion which is partially out of the target region location could be treated effectively and the accuracy and reliability of the tumor treatment are improved.

In the present embodiment, when the lesion is completely out of the target region, it is unnecessary to perform radiotherapy on the non-lesion portion in the current target region location. Instead, the intensity of ray beams may be adjusted by a ray beam intensity adjusting mechanism to a relatively small intensity or zero, thereby avoiding the radiotherapy on the non-lesion location and the damage to a normal part of the human body, and improving the safety and reliability of the tumor treatment. Further, the lesion location may be adjusted by the bed driving mechanism, or the target region location may be adjusted by a radiation source driving mechanism, such that in the next cycle or time period, the lesion completely falls within the target region location and receives the irradiation of ray beams having an adjusted predetermined intensity. Therefore, the tumor location could be precisely tracked, the radiotherapy location could be accurately adjusted, and therefore the lesion portion which is partially out of the target region location could be treated effectively and the accuracy and reliability of the tumor treatment are improved.

In the present embodiment, by means of the steps of receiving, by the detector, the scattering data when the ray beams of the radiation source pass through the lesion location, determining the relative location relationship between the lesion and the target region, and adjusting at least one of the intensity of ray beams, the lesion location and the target region location according to the relative location relationship between the lesion and the target region location, the lesion receives the irradiation of the ray beams having an adjusted predetermined intensity at the target region in the next cycle or time period. As such, fluctuations and errors in the intensity of the ray beams are avoided, and accurate therapy is achieved. Therefore, the tumor location could be precisely tracked, the radiotherapy location could be accurately adjusted, and thus the lesion portion which is partially or completely out of the target region location could be treated effectively, and the accuracy and reliability of the tumor treatment are improved.

In another embodiment of the present disclosure, the first detector further includes one or more second detector units configured to receive a portion of ray beams that are scattered when the ray beams pass through the lesion region, count according to photon energies, distinguish and classify the portion of received ray beams according to the photon energies, and acquire scattering data of the lesion region according to the classification result. Therefore, the photon energy distinguishing capability of the detector is achieved, the mutual interference among ray beams having various different photon energies is avoided, the accuracy and reliability of the scattering data as finally acquired are improved, and the accuracy and reliability of tracking the tumor location are also improved.

Figure 2:
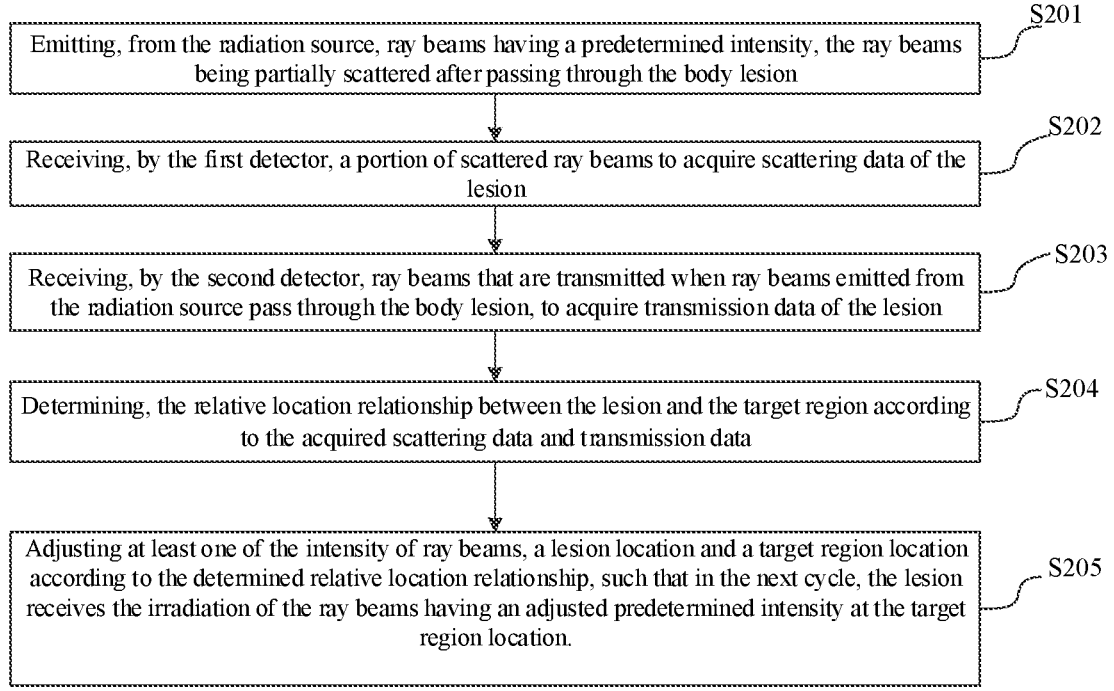
FIG. 2 is a schematic flowchart of a method for tracking tumor location according to another further embodiment of the present disclosure.

FIG. 2 is a schematic flowchart of a method for tracking tumor location according to another embodiment of the present disclosure. As shown in FIG. 2, the method for tracking tumor location, based on the above embodiment, includes the following steps S201-S205.

In step S201, the radiation source emits ray beams having a predetermined intensity, the ray beams being partially scattered after passing through the body lesion. In the implementations of the present disclosure, the radiation source may emit the ray beams periodically or continuously. In the case where the radiation source emits ray beams continuously, the rays emitted from the radiation source may be rays for radiotherapy. At this time, the first detector may receive, at a predetermined time interval, the ray beams emitted from the radiation source, or continuously receive the ray beams emitted from the radiation source.

In step S202, the first detector receives a portion of scattered ray beams to acquire scattering data of the lesion.

In step S203, the second detector receives ray beams that are transmitted when ray beams emitted from the radiation source pass through the body lesion, to acquire transmission data of the lesion.

In the present embodiment, the radiotherapy apparatus further includes a second detector. The radiation source, the body lesion and the second detector are located on a straight line. The second detector is a high-sensitivity optical detection device configured to receive ray beams that are transmitted when ray beams emitted from the radiation source pass through the body lesion, to acquire transmission data of the lesion, i.e., ray intensity data of the transmitted ray beams.

In step S204, the relative location relationship between the lesion and the target region is determined according to the acquired scattering data and transmission data.

In the present embodiment, by effectively combining the scattering data and the transmission data of the lesion, the relative location relationship between the lesion and the target region can be determined more accurately and accurately, and the accuracy and reliability of the tumor location tracking are improved.

In step S205, at least one of the intensity of ray beams, a lesion location and a target region location is adjusted according to the determined relative location relationship, such that in the next cycle, the lesion receives the irradiation of the ray beams having an adjusted predetermined intensity at the target region location.

In the present embodiment, by means of the steps of receiving, by the detector, the scattering data and the transmission data when the ray beams of the radiation source pass through the lesion location, determining the relative location relationship between the lesion and the target region, and adjusting at least one of the intensity of ray beams, the lesion location and the target region location according to the relative location relationship between the lesion and the target region, the lesion receives the irradiation of the ray beams having an adjusted predetermined intensity at the target region location in the next cycle. As such, fluctuations and errors in the intensity of the ray beams are avoided and accurate therapy is achieved. By effectively integrating the scattering data and transmission data of the lesion, the accuracy in tracking tumor location and adjusting radiotherapy location is improved. The lesion portions that are partially or completely out of the target region location could be effectively treated, and therefore, the accuracy and therapeutic effect on tumor treatment are promoted.

It should be noted that, in the embodiment of the present disclosure, by adjusting the lesion or target region location according to the determined relative location relationship, it specifically means that the lesion location in the next cycle is determined according to an image of the lesion and a movement trend of the lesion, thereby making the lesion in the next cycle inside the target region.

Figure 3:
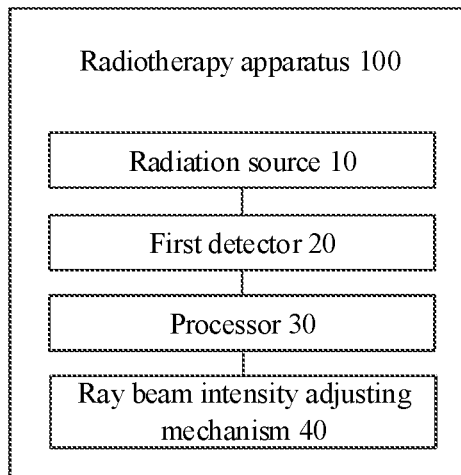
FIG. 3 is a schematic structural diagram of a radiotherapy apparatus according to an embodiment of the present disclosure.

FIG. 3 is a schematic structural diagram of a radiotherapy apparatus 100 in an embodiment of the present disclosure. As shown in FIG. 3, the radiotherapy apparatus 100, based on the above method embodiments, includes a radiation source 10, a first detector 20, a processor 30 and a ray beam intensity adjusting mechanism 40. The radiation source 10, a body lesion and the first detector 20 are not located on a straight line.

In the present embodiment, the radiotherapy apparatus may include one or more therapeutic heads. Each therapeutic head includes one or more radiation sources.

The radiation source may be a therapeutic radiation source, such as an isotope radiation source or an accelerator radiation source, that emits ray beams having a predetermined intensity to treat a lesion. The radiotherapy apparatus may further include a diagnostic radiation source, such as a bulb tube. The diagnostic radiation source may emit ray beams having a predetermined intensity in real time to image a lesion location. In some embodiments, the radiotherapy apparatus includes a plurality of therapeutic heads which could be used at different reference moments. For example, the reference using moments may be set to be spaced by a short time of 0.1 second, 0.2 second or 0.3 second to prevent the plurality of therapeutic heads from simultaneously emitting ray beams to interfere with each other.

In the present embodiment, the first detector 20 is a high-sensitivity optical detection device configured to receive a portion of ray beams that are scattered when ray beams emitted from the radiation source 10 pass through the body lesion, to acquire scattering data of the body lesion, that is, ray intensity data of the scattered ray beams. The first detector 20 includes one or more first detector units which are configured to receive ray beams respectively, and a filter unit. The detector acquires the scattering data of the lesion according to the ray beams received by each detector unit.

A radiotherapy apparatus provided by an embodiment of the present disclosure further includes a filter unit which corresponds to the one or more detector units. The filter unit may be a filter grid/lattice or a small-bore ray filter. Before the first detector 20 receives a portion of ray beams that are scattered when the ray beams pass through the lesion region, the ray beams may be filtered through the filter unit (the filter grid/lattice or the small-bore ray filter), such that the first detector unit receives the ray beams having specific scattering angles. As such, the spatial distinguishing capability of the detector is achieved, the mutual interference among ray beams at different scattering angles is avoided, the accuracy and reliability of the scattering data as finally acquired are improved, and the accuracy and reliability of tracking the tumor location are also improved.

In the present embodiment, the processor 30 includes an operation processing circuit configured to, according to the scattering data, i.e., ray intensity data of the scattered ray beams, acquired by the first detector 20, determine the relative location relationship between the lesion and the target region: the lesion completely falls within the target region, or is partially out of the target region or completely out of the target region, so as to subsequently determine whether the relative location relationship needs to be adjusted.

In the present embodiment, in the case where the radiation source is an accelerator, the ray beam intensity adjusting mechanism 40 is connected to the radiation source 10, and the intensity of the ray beams of the radiation source 10 is controlled by controlling a current. Alternatively, in the case where the radiation source is an isotope radiation source, such as a cobalt-60 radiation source, the ray beam intensity adjusting mechanism may be a filter layer or the like, which is configured to incompletely filter the ray beams, such that the ray beams having relatively low energies are emitted out. In the embodiment of the present disclosure, the specific structure of the ray beam intensity adjusting mechanism will not be defined specifically.

When the processor 30 determines that the lesion completely falls within the target region, the ray beam intensity adjusting mechanism 40 may correspondingly adjust the intensity of the ray beams of the radiation source 10 according to the intensity of the ray beams received by the lesion at the target region location in the previous one or two cycles, such that in the next cycle, the lesion receives the irradiation of the ray beams having an adjusted predetermined intensity at the target region location, thereby avoiding fluctuations and errors in the intensity of the ray beams and achieving precise treatment. When the processor 30 determines that the lesion is completely out of the target region, it is unnecessary to perform radiotherapy on the non-lesion portion in the current target region location. Instead, the intensity of ray beams in the next cycle may be adjusted by a ray beam intensity adjusting mechanism 40 to a relatively small intensity or zero, thereby avoiding the radiotherapy on the non-lesion location and the damage to a normal part of the human body, and improving the safety and reliability of the tumor treatment.

In the radiotherapy apparatus 100 of the present embodiment, the first detector 20 receives the scattering data when the ray beams of the radiation source 10 pass through the lesion location, the processor 20 determines the relative location relationship between the lesion and the target region, and the ray beam intensity adjusting mechanism 40 adjusts the intensity of ray beams according to the relative location relationship between the lesion and the target region determined by the processor 30, such that in the next cycle, the lesion receives the irradiation of the ray beams having an adjusted predetermined intensity at the target region location. Therefore, fluctuations and errors in the intensity of the ray beams are avoided, accurate therapy is achieved, and the accuracy and the therapeutic effect on tumor treatment are promoted. In the meantime, when the processor 30 determines that the lesion is completely out of the target region, the ray beam intensity adjusting mechanism 40 adjusts the intensity of the ray beams in the next cycle to be a relatively small intensity or zero, thereby avoiding the radiotherapy on the non-lesion location and the damage of a normal part of the human body, and improving the safety and reliability of the tumor treatment.

Figure 4:
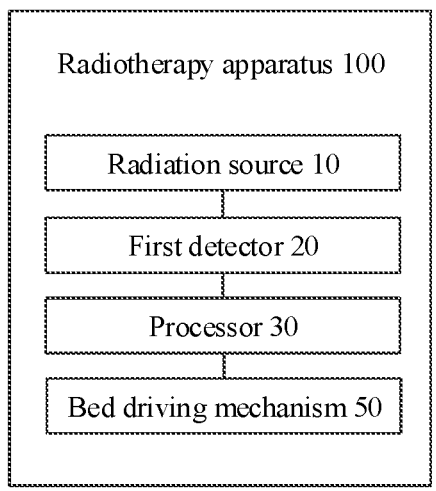
FIG. 4 is a schematic structural diagram of a radiotherapy apparatus according to another embodiment of the present disclosure.

FIG. 4 is a schematic structural diagram of a radiotherapy apparatus 100 in another embodiment of the present disclosure. As shown in FIG. 4, the radiotherapy apparatus 100 includes a radiation source 10, a first detector 20, a processor 30 and a bed driving mechanism 50. The radiation source 10, a body lesion and the first detector 20 are not located on a straight line.

In the present embodiment, the radiotherapy apparatus may include one or more therapeutic heads. Each therapeutic head includes one or more radiation sources. The radiation source may be a therapeutic radiation source, such as an isotope radiation source or an accelerator radiation source, that emits ray beams having a predetermined intensity to treat a lesion. The radiotherapy apparatus may further include a diagnostic radiation source, such as a bulb tube. The diagnostic radiation source may emit ray beams having a predetermined intensity in real time to image a lesion location. In some embodiments, the radiotherapy apparatus includes a plurality of therapeutic heads which could be used at different reference moments. For example, the reference using moments may be set to be spaced by a short time of 0.1 second, 0.2 second or 0.3 second to prevent the plurality of therapeutic heads from simultaneously emitting ray beams to interfere with each other.

In the present embodiment, the first detector 20 is a high-sensitivity optical detection device configured to receive a portion of ray beams of the radiation source 10, that are scattered when passing through the body lesion, to acquire scattering data of the body lesion, that is, ray intensity data of the scattered ray beams. The first detector 20 includes one or more first detector units which are configured to receive the scattered ray beams respectively. The detector acquires the scattering data of the lesion according to the ray beams received by each detector unit.

A radiotherapy apparatus provided by an embodiment of the present disclosure further includes a filter unit which corresponds to the one or more detector units. The filter unit may be a filter grid/lattice or a small-bore ray filter. Before the first detector 20 receives a portion of ray beams that are scattered when the ray beams pass through the lesion region, the ray beams may be filtered through the filter unit such as the filter grid/lattice or the small-bore ray filter, such that the first detector unit receives the ray beams having specific scattering angles. As such, the spatial distinguishing capability of the detector is achieved, the mutual interference among ray beams at different scattering angles is avoided, the accuracy and reliability of the scattering data as finally acquired are improved, and the accuracy and reliability of tracking the tumor location are also improved.

In the present embodiment, the processor 30 includes an operation processing circuit configured to, according to the scattering data, i.e., ray intensity data of the scattered ray beams, acquired by the first detector 20, determine the relative location relationship between the lesion and the target region: the lesion completely falls within the target region, or is partially out of the target region or completely out of the target region, so as to subsequently determine whether the relative location relationship needs to be adjusted.

In the present embodiment, the bed driving mechanism 50 is fixedly connected to a therapeutic bed and includes a linear or annular sliding rail structure. The linear or annular sliding rail structure is configured to drive the therapeutic bed to inline and move upwards, downwards, leftwards or rightwards to adjust the lesion location. When the processor 30 determines that the lesion is completely or partially out of the target region, the bed driving mechanism 50 may adjust the lesion location, such that in the next cycle, the lesion receives the irradiation of ray beams having an adjusted predetermined intensity within the target region location. Therefore, the tumor location could be precisely tracked, the radiotherapy location could be accurately adjusted, and therefore the lesion portion which is partially out of the target region location could be treated effectively and the accuracy and reliability of the tumor treatment are improved.

In the radiotherapy apparatus 100 of the present embodiment, the first detector 20 receives the scattering data when the ray beams of the radiation source 10 pass through the lesion location, the processor 20 determines the relative location relationship between the lesion and the target region, and the bed driving mechanism 50 adjusts the lesion location according to the relative location relationship between the lesion and the target region determined by the processor 30, such that in the next cycle, the lesion receives the irradiation of the ray beams having an adjusted predetermined intensity at the target region location. Therefore, the tumor location could be precisely tracked, the radiotherapy location could be accurately adjusted, and therefore the lesion portion which is partially out of the target region location could be treated effectively, and the accuracy and reliability of the tumor treatment are improved.

Figure 5:
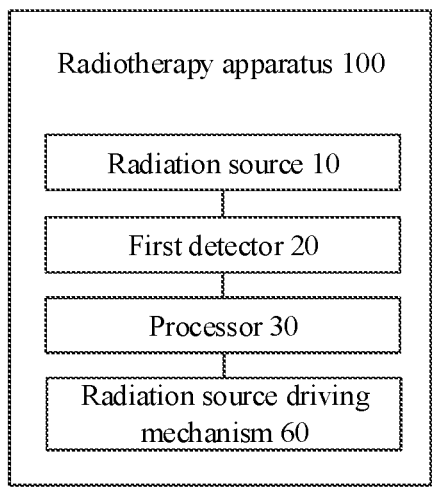
FIG. 5 is a schematic structural diagram of a radiotherapy apparatus according to a further embodiment of the present disclosure.

FIG. 5 is a schematic structural diagram of a radiotherapy apparatus 100 in a further embodiment of the present disclosure. As shown in FIG. 5, the radiotherapy apparatus 100 includes a radiation source 10, a first detector 20, a processor 30 and a radiation source driving mechanism 60. The radiation source 10, a body lesion and the first detector 20 are not located on a straight line.

In the present embodiment, the radiotherapy apparatus may include one or more therapeutic heads. Each therapeutic head includes one or more radiation sources. The radiation source may be a therapeutic radiation source, such as an isotope radiation source or an accelerator radiation source, that emits ray beams having a predetermined intensity to treat a lesion. The radiotherapy apparatus may further include a diagnostic radiation source, such as a bulb tube. The diagnostic radiation source may emit ray beams having a predetermined intensity in real time to image a lesion location. In some embodiments, the radiotherapy apparatus includes a plurality of therapeutic heads which could be used at different reference moments are different. For example, the reference using moments may be set to be spaced by a short time of 0.1 second, 0.2 second or 0.3 second to prevent the plurality of therapeutic heads from simultaneously emitting ray beams to interfere with each other.

In the present embodiment, the first detector 20 is a high-sensitivity optical detection device configured to receive a portion of ray beams of the radiation source 10, that are scattered when passing through the body lesion, to acquire scattering data of the body lesion, that is, ray intensity data of the scattered ray beams. The first detector 20 includes one or more first detector units which are configured to receive the scattered ray beams respectively. The detector acquires the scattering data of the lesion according to the ray beams received by each detector unit.

A radiotherapy apparatus provided by an embodiment of the present disclosure further includes a filter unit which corresponds to the one or more detector units. The filter unit may be a filter grid/lattice or a small-bore ray filter. Before the first detector 20 receives a portion of ray beams that are scattered when the ray beams pass through the lesion region, the ray beams may be filtered through the filter unit such as the filter grid/lattice or the small-bore ray filter, such that the first detector unit receives the ray beams having specific scattering angles. As such, the spatial distinguishing capability of the detector is achieved, the mutual interference among ray beams at different scattering angles is avoided, the accuracy and reliability of the scattering data as finally acquired are improved, and the accuracy and reliability of tracking the tumor location are also improved.

In the present embodiment, the processor 30 includes an operation processing circuit configured to, according to the scattering data, i.e., ray intensity data of the scattered ray beams, acquired by the first detector 20, determine the relative location relationship between the lesion and the target region: the lesion completely falls within the target region, or is partially out of the target region or completely out of the target region, so as to subsequently determine whether the relative location relationship needs to be adjusted.

In the present embodiment, the radiation source driving mechanism 60 is fixedly connected to a radiation source 10 and includes a linear or annular sliding rail structure. The linear or annular sliding rail structure is configured to drive the radiation source 10 to move to adjust the target region location. When the processor 30 determines that the lesion is completely or partially out of the target region, the radiation source driving mechanism 60 may adjust the target region location, such that in the next cycle, the lesion receives the irradiation of ray beams having an adjusted predetermined intensity within the target region location. Therefore, the tumor location could be precisely tracked, the radiotherapy location could be accurately adjusted, and therefore the lesion portion which is partially out of the target region location could be treated effectively and the accuracy and reliability of the tumor treatment are improved.

In the radiotherapy apparatus 100 of the present embodiment, the first detector 20 receives the scattering data when the ray beams of the radiation source 10 pass through the lesion location, the processor 20 determines the relative location relationship between the lesion and the target region, and the radiation source driving mechanism 60 adjusts the target region location according to the relative location relationship between the lesion and the target region determined by the processor 30, such that in the next cycle, the lesion receives the irradiation of the ray beams having an adjusted predetermined intensity at the target region location. Therefore, the tumor location could be precisely tracked, the radiotherapy location could be accurately adjusted, and therefore the lesion portion which is partially out of the target region location could be treated effectively and the accuracy and reliability of the tumor treatment are improved.

In a further embodiment of the present disclosure, the processor 30 is further configured to receive a portion of ray beams that are scattered when the ray beams of the radiation source 10 pass through the lesion region, count according to photon energies, distinguish and classify the portion of received ray beams according to the photon energies, and acquire scattering data of the lesion region according to the classification result. Therefore, the photon energy distinguishing capability of the detector is achieved, the mutual interference among ray beams having various different photon energies is avoided, the accuracy and reliability of the scattering data as finally acquired are improved, and the accuracy and reliability of tracking the tumor location are also improved.

In another embodiment of the present disclosure, the radiotherapy apparatus 100, based on the above embodiments, further includes a second detector. The radiation source 10, the body lesion and the second detector are located on a straight line. The second detector is a high-sensitivity optical detection device configured to receive ray beams that are transmitted when ray beams emitted from the radiation source 10 pass through the body lesion, to acquire transmission data of the lesion, i.e., ray intensity data of the transmitted ray beams. In the present embodiment, by effectively integrating the scattering data and the transmission data of the lesion acquired by the first detector 20 and the second detector, the relative location relationship between the lesion and the target region may be determined more precisely and accurately, and the accuracy and reliability of the tumor location tracking are improved.

It should be understood that various portions of the present disclosure may be implemented by hardware, software, firmware, or a combination thereof. In the above embodiments, a plurality of steps or methods may be implemented with software or firmware that are stored in the memory and executed by a suitable instruction execution system. For example, when implemented with hardware, as is in other embodiments, it could be implemented by using any one or a combination of the following techniques well known in the art: a discrete logic circuit with a logic gate circuit having logic gates for implementing logic functions upon data signals, an application-specific integrated circuit with a suitable combinational logic gate circuit, a programmable gate array (PGA), a field programmable gate array (FPGA), and the like.

In the description of the present specification, the description of terms such as "an embodiment", "some embodiments", "an example", "a specific example" and "some examples" means that the particular features, structures, materials or characteristics as described by combining the specific embodiments or examples are included in at least one embodiment or example of the present disclosure. In the specification of the present disclosure, schematic description of the above terms does not necessarily refer to the same embodiment or example. Furthermore, the described particular features, structures, materials or characteristics can be integrated with any one or more embodiments or examples in a proper manner.

Although the embodiments of the present disclosure have been shown and described, it should be understood by those skilled in the art that various changes, modifications, substitutions and variations of theses embodiments may be made without departing from the principle and spirit of the present disclosure. The scope of the present disclosure is defined by the appended claims and equivalents thereof.

What is claimed is:

1. A method for tracking tumor location applied to a radiotherapy apparatus, comprising:
    providing the radiotherapy apparatus comprising a first detector, a second detector and at least one radiation source, wherein the radiation source, the body lesion and the second detector are located on a straight line;
    emitting, from the radiation source, ray beams having a predetermined intensity, the ray beams being partially scattered after passing through the body lesion;
    receiving, by the first detector, a portion of scattered ray beams that are scattered when the ray beams pass through the body lesion;
    distinguishing and classifying the received portion of scattered ray beams based on energy;
    acquiring a scattering data of the body lesion according to the classification result;
    receiving, by the second detector, the ray beams that pass through the body lesion and acquiring a ray intensity data of the transmitted ray beams;
    determining a relative location relationship between the body lesion and the target region according to the acquired scattering data and the ray intensity data of the transmitted beams;
    determining whether the body lesion is at least partially out of a target region based on the acquired scattering data;
    adjusting at least one of the intensity of ray beams, a body lesion location and a target region location when the body lesion is at least partially out of the target region, such that the body lesion receives the irradiation of the ray beams having an adjusted predetermined intensity at the target region location.

2. The method for tracking tumor location according to claim 1, wherein:
    the first detector comprises one or more first detectors; and
    the method, prior to said receiving, by the one or more first detectors, a portion of scattered ray beams to acquire scattering data of the body lesion, further comprises: filtering the ray beams, such that a specific first detector receives the ray beams having specific scattering angles.

3. The method for tracking tumor location according to claim 1, wherein the at least one radiation source is a therapeutic radiation source.

4. The method for tracking tumor location according to claim 1, wherein the at least one radiation source comprises at least one therapeutic radiation source and at least one diagnostic radiation source.

5. The method for tracking tumor location according to claim 1, wherein when the radiation source comprises a plurality of radiation sources, the plurality of radiation sources are used at different reference moments.

6. A radiotherapy apparatus, comprising:
    a first detector, a second detector and at least one radiation source;
    at least one of a ray beam intensity adjusting mechanism, a bed driving mechanism and a radiation source driving mechanism, wherein the radiation source, the body lesion and the second detector are located on a straight line;
    the radiation source is configured to emit ray beams having a predetermined intensity, the ray beams being partially scattered after passing through the body lesion;
    the first detector is configured to receive a portion of scattered ray beams to acquire scattering data of a lesion region;
    the second detector is configured to receive ray beams that are transmitted when the ray beams emitted from the radiation source pass through the body lesion, and to acquire a ray intensity data of the transmitted ray beams;
    a processor configured to distinguish and classify the scattered ray beams received by the first detector unit based on energy, acquire a scattering data of the body lesion according to the classification result, determine a relative location relationship between the body lesion and the target region according to the acquired scattering data and the ray intensity data of the transmitted ray beams, and determine whether the body lesion is at least partially out of a target region according to the scattering data acquired by the first detector;
    the ray beam intensity adjusting mechanism is configured to adjust the intensity of ray beams when the body lesion is at least partially out of the target region;
    the bed driving mechanism is configured to adjust a body lesion location when the body lesion is at least partially out of the target region; and
    the radiation source driving mechanism is configured to adjust a target region location when the body lesion is at least partially out of the target region.

7. The radiotherapy apparatus according to claim 6, wherein:
- the first detector comprises one or more first detectors; and
- the radiotherapy apparatus further comprises a filter configured to filter the scattered ray beams, such that a specific first detector receives the scattered ray beams having specific scattering angles.

8. The radiotherapy apparatus according to claim 6, wherein the at least one radiation source is a therapeutic radiation source.

9. The radiotherapy apparatus according to claim 6, wherein the at least one radiation source comprises at least one therapeutic radiation source and at least one diagnostic radiation source.

* * * * *